United States Patent [19]

Farling

[11] Patent Number: 4,997,444
[45] Date of Patent: Mar. 5, 1991

[54] IMPLANT HAVING VARYING MODULUS OF ELASTICITY

[75] Inventor: Gene M. Farling, Warsaw, Ind.

[73] Assignee: Zimmer, Inc., Warsaw, Ind.

[21] Appl. No.: 458,462

[22] Filed: Dec. 28, 1989

[51] Int. Cl.⁵ .............................. A61F 2/28; A61F 2/32
[52] U.S. Cl. ........................................... 623/16; 623/23
[58] Field of Search ....................... 623/16, 18, 19, 20, 623/22, 23

[56] References Cited

U.S. PATENT DOCUMENTS

| | | | |
|---|---|---|---|
| 3,623,164 | 11/1971 | Bokros | 3/1 |
| 3,781,917 | 1/1974 | Mathys | 3/1 |
| 3,906,550 | 9/1975 | Rostoker et al. | 3/1.912 |
| 3,979,779 | 9/1976 | Zeibig et al. | 3/1.91 |
| 4,051,559 | 10/1977 | Pifferi | 3/1.912 |
| 4,266,302 | 5/1981 | Tornier | 3/1.912 |
| 4,292,694 | 10/1981 | Koeneman | 3/1.91 |
| 4,292,695 | 10/1981 | Koeneman | 3/1.91 |
| 4,314,381 | 2/1982 | Koeneman | 3/1.912 |
| 4,479,271 | 10/1984 | Bolesky et al. | 3/1.911 |
| 4,488,319 | 12/1984 | von Recum | 3/1.913 |
| 4,516,277 | 5/1985 | Butel | 3/1.913 |
| 4,536,894 | 8/1985 | Galante et al. | 623/22 |
| 4,608,055 | 8/1986 | Morrey et al. | 623/23 |
| 4,619,659 | 10/1986 | Witzel | 623/23 |
| 4,676,797 | 6/1987 | Anapliotis et al. | 623/18 |
| 4,681,590 | 7/1987 | Tansey | 623/23 |
| 4,743,263 | 5/1988 | Petrtyl et al. | 623/23 |
| 4,752,296 | 6/1988 | Buechel et al. | 623/23 |
| 4,756,711 | 7/1988 | Mai et al. | 623/23 |
| 4,808,186 | 2/1989 | Smith | 623/23 |
| 4,813,963 | 3/1989 | Hori et al. | 623/23 |
| 4,828,566 | 5/1989 | Griss | 623/23 |
| 4,851,007 | 7/1989 | Gray | 623/23 |
| 4,878,919 | 11/1989 | Pavlansky et al. | 623/22 |
| 4,938,770 | 7/1990 | Frey et al. | 623/23 |

FOREIGN PATENT DOCUMENTS

| | | |
|---|---|---|
| 0220803A2 | 5/1987 | European Pat. Off. . |
| 0243298A2 | 10/1987 | European Pat. Off. . |
| 0257359A1 | 3/1988 | European Pat. Off. . |
| 0273871A1 | 7/1988 | European Pat. Off. . |
| 0289922A1 | 11/1988 | European Pat. Off. . |
| 2425237 | 12/1979 | France . |
| 2475892 | 8/1981 | France . |
| WO89/7424 | 8/1989 | PCT Int'l Appl. . |

OTHER PUBLICATIONS

Zimmer, Inc. brochure—Harris/Galante Porous Hip Prosthesis—Lit. No. 97-6520-01, 1986.

*Primary Examiner*—David J. Isabella
*Attorney, Agent, or Firm*—Margaret L. Geringer

[57] ABSTRACT

An implant is disclosed which includes an elongated portion constructed in such a manner that the modulus of elasticity varies from one end to another. A plurality of discs alternating between solid discs and mesh discs are stacked with the relationship between the composite thickness of mesh regions as compared to the thickness of solid regions determining the modulus of elasticity at any region thereof. The invention is applicable to all different types of prosthetic implants.

24 Claims, 3 Drawing Sheets

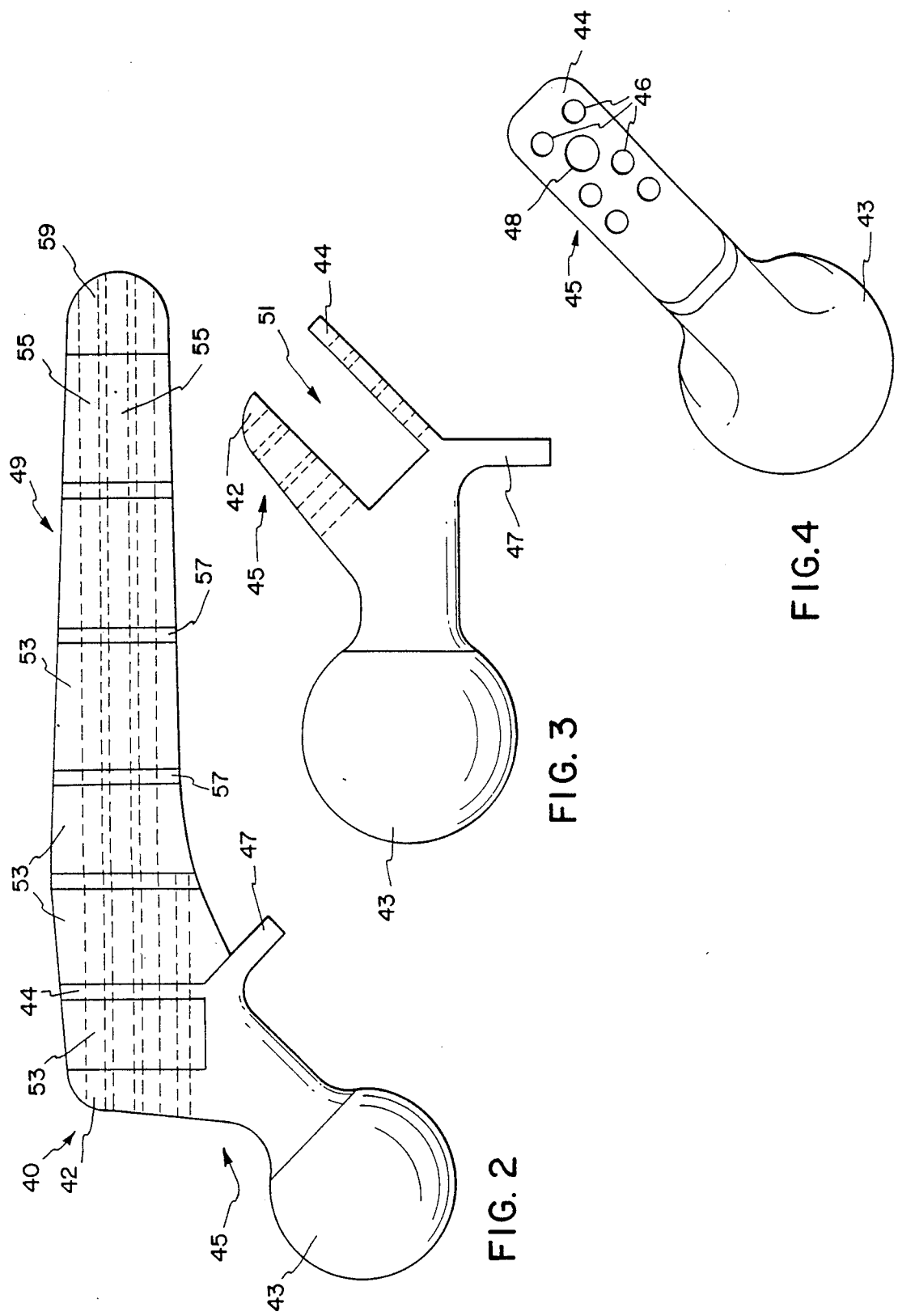

IMPLANT HAVING VARYING MODULUS OF ELASTICITY

BACKGROUND OF THE INVENTION

The present invention relates to an implant having varying modulus of elasticity. In the prior art, structures exist which either inherently or intentionally act to vary the modulus of elasticity along a desired length. However, Applicant is unaware of any such structure which includes all of the features of the present invention and acts to vary the modulus of elasticity of an elongated stem-like structure with the effectiveness of the present invention.

The following prior art is known to Applicant:

U.S. Pat. No. 3,906,550 to Rostoker, et al. discloses a prosthetic device having a porous fiber metal structure. As best seen in FIG. 1 thereof, a plurality of tubular fiber-metal segments are disposed on a single elongated rod 24 and are provided to facilitate bony ingrowth along a large surface area. The present invention differs from the teachings cf Rostoker, et al. for reasons including the interpositioning of solid metallic discs between regions of fiber metal discs.

U.S. Pat. No. 4,051,559 to Pifferi discloses a prosthesis including a plurality of components assembled together to form the prosthesis. As seen in FIGS. 1 and 3 in particular, a stem 1 is attached to a head 5, 6, 7 through the use of an elongated bolt-like fastener 4. The present invention differs from the teachings of Pifferi for reasons including the use of regions of fiber metal discs separated by solid metallic discs.

U.S. Pat. No. 4,292,695 to Koeneman discloses a prosthesis stem including a stem portion formed in the shape of the medullary canal of a particular bone and including a plurality of individual sections of a resilient generally circular layer of elastomeric material 15 bonded in alternating fashion to a correspondingly shaped but rigid layer 17 made of a metallic alloy. The present invention differs from the teachings of Koeneman for reasons including the fact that the regions of the present invention composed of fiber metal may be varied as to their respective thicknesses between respective solid metallic discs to vary the modulus of elasticity of the stem portion thereof along its length.

U.S. Pat. No. 4,266,302 to Tornier discloses a femoral pin including a hilt member from which a plurality of funicular elements extend. The present invention differs from the teachings of Tornier for reasons including the fact that the present invention contemplates stacking of components of the prosthesis on top of one another rather than providing such components in a side-to-side configuration as is the case with Tornier.

U.S. Pat. No. 4,314,381 to Koeneman discloses a hip joint prosthesis having an elongated stem having mounted thereon radially outwardly protruding rings 35 and spacers 37, with the rings being made of an elastomeric material and with the spacers being made of a metallic alloy. The present invention differs from the teachings of Koeneman as contemplating a stacked relationship between rigid and less rigid components as compared to the radial spacing of the Koeneman components.

U.S. Pat. No. 4,743,263 to Petrtyl, et al. discloses a prosthesis which is similar to the teachings of Tornier, discussed above, as including a plurality of strands of material emanating from a single hilt. The present invention differs from the teachings of Petrytyl, et al. for the same reasons set forth above concerning Tornier.

U.S. Pat. No. 4,808,186 to Smith discloses an implant having an elongated stem with a longitudinal channel therein. The thickness of the stem laterally of the channel is variable between the proximal and distal ends to achieve stem flexibility which substantially correlates to the flexibility of the bone. The present invention differs from the teachings of Smith for reasons including the interpositioning of solid metallic discs between regions of fiber metal discs.

European Patent Application No. 0 220 803 to Brooks, et al. discloses a prosthesis including a cushioning body 15 interposed between the head 13 thereof and the elongated stem 11 thereof. The present invention differs from the teachings of Brooks, et al. as contemplating a variability in the modulus of elasticity of an elongated stem component throughout its length.

French Patent No. 2 425 237 to Breard discloses a prosthesis including, in a manner similar to the teachings of Tornier and Petrytyl, et al. discussed above, a plurality of strands of material designated by the reference numeral 9 in FIG. 6, for example, emanating from a single location. Again, the present invention differs from the teachings of Breard for the same reasons discussed hereinabove with regard to Tornier.

It is a known fact that live bone continuously changes in response to the demands and forces placed on it. Thus, a well designed prosthesis should include consideration of factors allowing duplication of the properties of the bone which is adjacent the prosthesis.

A prosthesis should transmit load evenly and over a large area while at the same time distributing continuous stress to the adjacent bone sufficient to encourage healthy bone formation throughout the interface therebetween (for a prosthesis of the type that is adapted for bony ingrowth, as with a porous material such as with a porous fiber metal structure). Thus, it is desired to provide a prosthesis which includes variations in the modulus of elasticity in different regions thereof, excellent fatigue properties, and maximum exposure of the bony ingrowth regions thereof to best facilitate bony ingrowth.

The present invention seeks to provide a prosthesis which:

(1) is less rigid than many of the presently manufactured prostheses;

(2) incorporates load transmission patterns which are designed to conform to normal bone characteristics;

(3) optimizes the area of bony ingrowth to enhance securement of the prosthesis to the bone, and thus lessen the possibility of prosthesis loosening and provide more even stress distribution.

SUMMARY OF THE INVENTION

The present invention relates to an implant having varying modulus of elasticity. The present invention includes the following interrelated aspects and features:

(a) In a first aspect, the principles of the present invention may be applied to any prosthesis, whether intended for implantation in the knee, hip, wrist, elbow, shoulder, or other location. Wherever the prosthesis is intended to be implanted, the principles of the present invention may be utilized to tailor the characteristics of the prosthesis to the contemplated environment of implantation.

(b) The inventive prosthesis includes an elongated stem depending from a neck or head or base portion.

The example used in this patent application is that of a femoral head hip prosthesis having a head connected to a neck from which depends an elongated stem component. It is the details of the stem component which form the main examples of the teachings of the present invention.

(c) The details of the stem component include, in the preferred embodiment thereof, a main centrally located elongated strut surrounded by a plurality of smaller struts of differing lengths. All of these struts are connected at their respective proximal ends to the head or stem or base portion of the prosthesis.

(d) A plurality of solid metallic discs and fiber metal discs are provided with holes therethrough corresponding to the respective locations of the struts so that these discs may be assembled thereover. These discs are assembled over the struts in an alternating fashion with single solid metallic discs being separated from one another by desired numbers of fiber metal discs. In one embodiment, all of the fiber metal discs are of substantially the same thickness and, from the proximal end of the stem component to the distal end thereof, the number of fiber metal discs interposed between respective solid metallic discs is sequentially increased to sequentially increase the flexibility of the stem component from the proximal end toward the distal end. Alternatively, the thicknesses of the fiber metal discs could be varied in such a manner that with equal numbers of fiber metal discs interposed between respective ones of the solid metallic discs, the thickness of fiber metal between respective ones of the solid metallic discs would increase from the proximal end to the distal end. Of course, these configurations are but examples of the manner of implementation of the teachings of the present invention The thickness of fiber metal material between various ones of the solid metallic discs may be varied in a manner so as to vary the modulus of elasticity of the stem component in any desired manner.

(e) A solid metallic end cap may be provided to lock all of the discs on the struts. If desired, for this purpose, the main centrally located strut may have a threaded end and the end cap may have a complimentary threaded recess. Of course, any suitable attachment means between the end cap and the main strut may be employed.

(f) Of course, all of the materials of the inventive stem component should be made of biocompatible materials. Titanium alloys have been found to be effective for use in making the solid metallic portions such as the base portion, the struts, the solid metallic discs, and the end cap, while commercially pure titanium has been found to be effective for use in making the fiber metal discs. Of course, any other suitable biocompatible metals and metallic alloys may be employed.

(g) In a further aspect, through variation in the outer dimensions of the respective discs or plates, the stem component as created therefrom may be made to have any desired outer dimensions. Thus, by slightly reducing the outer dimensions of each disc or plate from the proximal end to the distal end, a tapered stem component taking on a truncated conical configuration may be created. Of course, any desired outward configuration may be created through variations in the dimensions of the respective discs or plates.

As such, it is a first object of the present invention to provide an implant having varying modulus of elasticity.

It is a further object of the present invention to provide such an implant having variation in the modulus of elasticity which is created through alternation of solid metallic discs or plates with fiber metal discs or plates in a stem component of a prosthesis.

It is a yet further object of the present invention to vary the outward configuration of such a stem component by variations in the dimensions of individual discs or plates.

It is a still further object of the present invention to support such discs or plates on a stem component through the use of struts of differing thicknesses and lengths.

It is a still further object of the present invention to assemble a multiplicity of such discs or plates together to form a stem component which is retained in assembly through the use of a suitable end cap.

These and other objects, aspects and features of the present invention will be better understood from the following detailed description of the preferred embodiments when read in conjunction with the appended drawing figures.

BRIEF DESCRIPTION OF THE DRAWINGS

FIG. 2 shows a side view of a second embodiment of the present invention.

FIG. 3 shows a side view of the head component of the embodiment of FIG. 2.

FIG. 4 shows a view of the head component of FIG. 3 rotated 90 degrees from the view of FIG. 3.

SPECIFIC DESCRIPTION OF THE PREFERRED EMBODIMENTS

Figure 1:
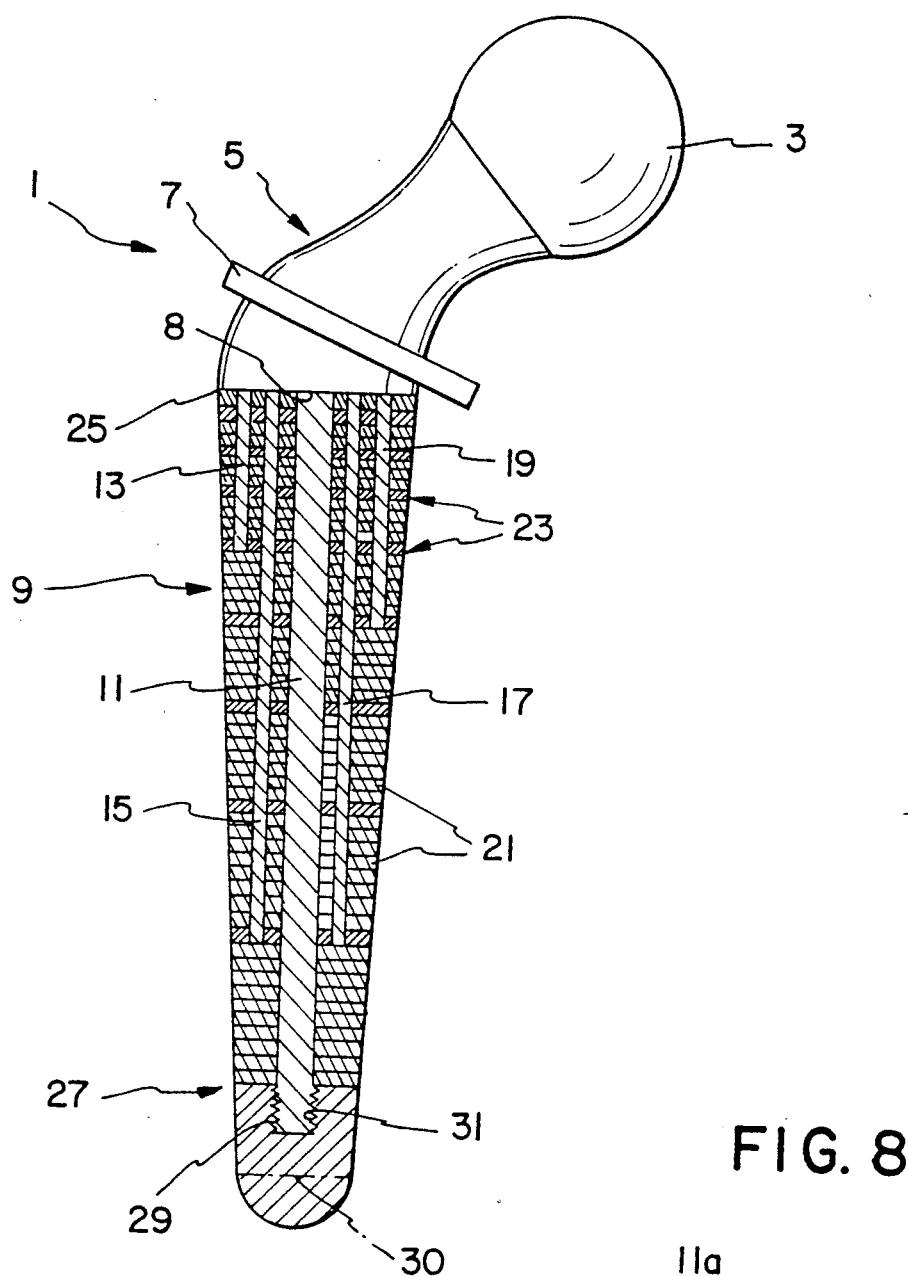
FIG. 1 shows a side view of an example of a prosthesis made in accordance with the teachings of the present invention with a cross-section through the stem component thereof.
Figure 8:
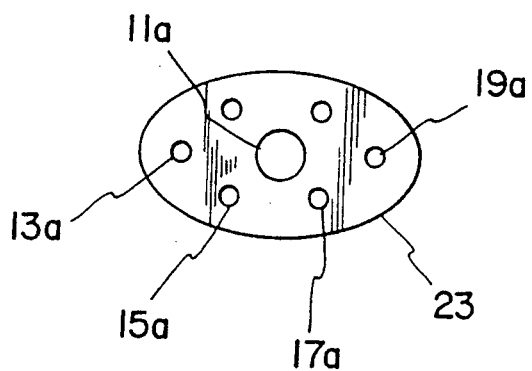
FIG. 8 shows an end view of one of the discs of the embodiment of FIG. 1.

With reference, first, to FIGS. 1 and 8, a hip prosthetic component is generally designated by the reference numeral 1 and is seen to include a head 3, a neck portion 5 having a collar 7, and a stem component 9 depending from a shoulder 8 or base portion of the neck portion of the prosthesis 1.

A main strut 11 centrally depends from the shoulder 8 as do smaller struts 13, 15, 17 and 19. Two additional struts are not seen in the view of FIG. 1, but their location will be better understood in the discussion hereinbelow concerning FIG. 8.

The struts 11, 13, 15, 17, 19 and the two struts not shown in FIG. 1 are attached to the neck portion 5 shoulder 8 by any suitable means. Examples of means of attachment of the struts to the neck portion 5 include providing the struts with threaded ends which may be threaded into correspondingly threaded recesses in the neck portion, as well as sintering of the struts through the use of blind bores (not shown) in the neck portion into which proximal ends of the struts are inserted and thereafter sintered or otherwise suitably metallurgically bonded.

As seen in FIG. 1, the stem component 9 is composed of a multiplicity of fiber metal discs 21 along with a multiplicity of solid metallic discs 23. In the embodiment of FIG. 1, each of the discs 21 is of like thickness to other ones of the discs 21, as is the case with the solid metallic discs 23. As shown in FIG. 1, the discs 21, 23 are assembled on the struts in a pattern designed to vary the modulus of elasticity along the length of the stem component 9.

In particular, adjacent the shoulder 8 of the neck portion 5, a single fiber metal disc 21 is provided after which a solid metallic disc 23 is assembled over the struts. Thereafter, two fiber metal discs 21 are followed by a single solid metallic disc 23 after which three fiber metal discs 21 are stacked over the struts followed by a further single solid metallic disc, and so on. Thus, as one travels from the proximal end 25 of the stem component to the distal end 27 thereof, the solid metallic discs 23 are spaced further and further apart from one another by increasingly taller stacks of fiber metallic discs 21. Since the fiber metal discs 21 are more flexible than the solid metallic discs 23, as one travels from the proximal end 25 to the distal end 27 of the stem component 9, the stem component 9 becomes more and more flexible in that direction, thus decreasing the modulus of elasticity in that direction. Of course, this is merely one example of a configuration of the respective discs 21 and 23 which may be employed in a stem component. Any desired configuration of the respective solid metallic discs 23 and fiber metal discs 21 may be employed so as to result in the desired degree of elasticity of a stem component in its various regions.

As shown in FIG. 1, the respective lengths of the struts is specifically designed so that individual struts terminate at a solid metallic disc 23 so that firm attachment of the termination of a strut to a solid metallic disc 23 may be carried out by any suitable method such as, for example, sintering. The main centrally located strut 11 may include a threaded end 29 over which may be threaded the correspondingly threaded recess 31 of an end cap 30.

With reference to FIG. 8, a single disc 23 is seen to include openings therethrough designated by the reference numerals 11a, 13a, 15a, 17a and 19a to correspond with the respectively numbered struts 11, 13, 15, 17 and 19. The two unnumbered openings in the disc 23 illustrated in FIG. 8 show the location of the struts not illustrated in FIG. 1. The fiber metal discs 21 would also include correspondingly located openings (not shown).

The preferred materials for use in constructing the inventive prosthesis 1 would be those materials which have been found to be biocompatible in implant situations. For example purposes only, the stem component 9 may be composed of various biocompatible materials including, but not limited to, titanium fiber mesh for the fiber metal discs 21, solid titanium alloy for the solid metallic discs 23, and titanium alloys for the struts and end cap. Again, these material choices are merely exemplary and any materials which are found to have sufficient strength to be used in the implant environment and which have been found to be biocompatible may be employed. It is important to note the great surface area of exposure of the outer peripheries of the fiber metal discs 21. This large total surface area best promotes bony ingrowth when the prosthesis 1 is implanted.

The fiber metal discs 21 may be manufactured from a porous fiber metal structure such as that described by U.S. Pat. No. 3,906,550 (noted in Background section), although any suitable fiber metal structure may be utilized. The fiber metal material may be compressed and molded and/or cut into the desired shape, as appropriate. The solid metal portions of the implant or prosthesis 1 may be manufactured by any suitable means. All of the individual solid and porous components are assembled together in the desired configuration. The components may be mechanically secured together in some instances, as previously described, such as via threaded components, and all of the components may be metallurgically bonded together by sintering or other appropriate metallurgical bonding method. However, a bonding method, such as sintering, which can securely bond all of the prosthesis components together to become a single unit is preferable. Sintering is a heat-treatment process which metallurgically bonds metals together. This prosthesis would be sintered together after assembly.

Again, the configuration relationship between the fiber metal discs 21 and the solid metallic discs 23 is merely exemplary. Should one not wish to vary the modulus of elasticity of the stem component 9 from one end to another, equal numbers of fiber metal discs may be interposed between respective pairs of solid metallic discs. Any desired pattern of numbers of fiber metal discs 21 interposed between respective pairs of solid metallic discs 23 may be employed depending upon the particular situation.

With reference, now, to FIGS. 2-7 and 9, a further embodiment of the present invention is generally designated by the reference numeral 40 and is seen to include a head portion 43, a neck portion 45 having a collar 47, and a stem component generally designated by the reference numeral 49.

With particular reference to FIGS. 3 and 4, the head portion 43 and neck portion 45 are formed of a single piece including two substantially parallel plate-like extensions 42 and 44. The plate-like extensions 42 and 44 form a shoulder or base portion from which struts 55 depend. (It is understood that the head may be separate from the neck as is well known in the art of modular hip prostheses, although not shown as such.) An end view of the plate-like portion 44 is seen in FIG. 4 to include a plurality of openings 46 therethrough as well as a large central opening 48. Openings corresponding to these openings 46, 48 are also formed in the plate-like portion 42. These aligned openings are provided to allow longitudinal alignment of struts 55 therebetween. The chamber 51 formed between the plate-like portions 42 and 44 is sized and configured to receive one or more fiber metal segments 53 which are inserted within the chamber 51 prior to installation of the struts 55.

In the embodiment of FIG. 2, the stem component 49 includes spaced plate-like portions 42 and 44 and plates 57 each sequentially spaced an increasing distance apart from each other. The fiber metal segments 53 which are positioned therebetween are each preferably a single-piece fiber metal segment between each metal plate layer, such that each sequential fiber metal segment 53 increases in thickness as the stem 49 progresses from the proximal end to the distal end (as opposed to the embodiment of FIG. 1 wherein fiber metal discs 21 of similar thickness are varied in number of discs 21 between repetitive metallic discs 23). Although both embodiments of FIGS. 1 and 2 are contemplated by the present invention, the embodiment of FIG. 2 utilizing the single fiber metal segments of varied thickness would be preferable over the multiple fiber metal discs 21 between metal discs 23 to lessen the number of assembled components.

As seen in FIG. 2, fiber metal segments 53 are provided of shapes designed to create the outer shape of the assembled prosthesis, with solid metallic plates 57 being interposed therebetween in a desired configuration.

Figure 6:
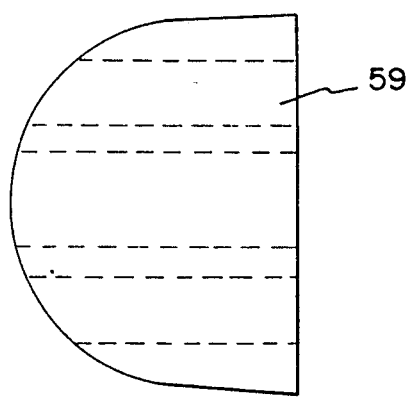
FIG. 6 shows a side view of the end cap of FIG. 5.
Figure 5:
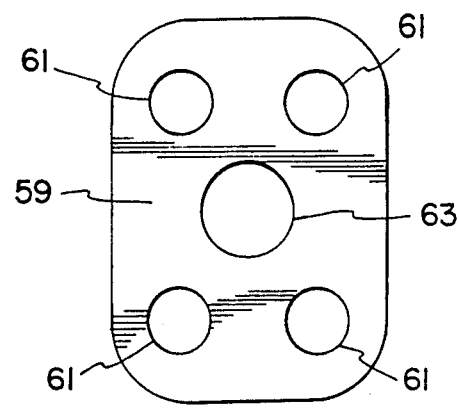
FIG. 5 shows a top view of the end cap of the embodiment of FIG. 2.
Figure 7:
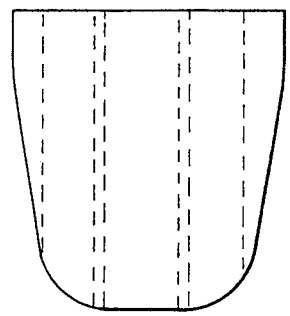
FIG. 7 shows a further side view rotated 90 degrees from the view of FIG. 6.

An end cap 59 may be installed over the ends of the struts in any desired manner such as through sintering or through use of some biocompatible adhesive or other suitable bonding means. With reference to FIGS. 5, 6 and 7, since a plurality of the struts extend all the way through the stem component 49 and enter recesses 61, 63 of the end cap 59, the end cap 59 may not be attached to the struts through a threaded connection, as is the case in the embodiment of FIGS. 1 and 8, wherein only the main strut 11 extends to the end cap 30.

Figure 9:
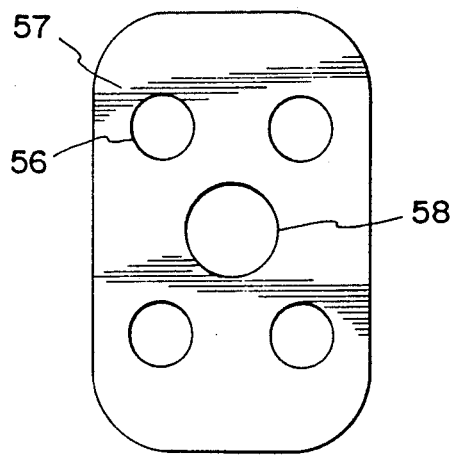
FIG. 9 shows an end view of one of the plates of the embodiment of FIGS. 2-7.

FIG. 9 shows one of the plates 57 to illustrate an example of the general outer configuration thereof as being somewhat rectangular with rounded corners. The openings 56, 58 extending through the plate 57 align with corresponding openings formed through the fiber metal segments 53 and the other plates 57 to provide a continuous elongated passage for each strut 55.

As should be understood from review of both embodiments disclosed hereinabove, the particular shape of the entirety of the outer surface of the stem component 9 or 49 may be made in any desirable manner by designing the respective outer configurations of each of the discs, whether solid metallic discs or fiber metal discs, to result in the desired outer configuration in assembly. The fiber metal and solid metallic structures can be varied in design. The outer edges of the fiber metal structures may be flush with the outer edges of the solid metallic structures as shown in FIGS. 1 and 2 or the cross-section of the solid metallic structures may be slightly smaller than the cross-section of the fiber metal structure such that the solid metallic portions are slightly recessed relative to the fiber metal structures (not shown). The solid metallic structures may be further recessed to allow the fiber metal structures to include an extending lip to cover the recessed edge of the solid metallic structures to give the stem portion the appearance of a complete fiber metal outer surface for increased surface area for bony ingrowth (not shown).

In addition, with regard to both embodiments, it is noted that the struts may be made in any number of configurations. They may vary in diameter and length, may be straight or tapered, or may be machined or formed as an integral part of the shoulder section. The struts may be used in any suitable combination, as desired. The size, style, and number of struts along with the cross-sectional area of the prosthesis are determined in conjunction with the number and placement of the fiber metal and solid metallic structures.

Furthermore, while the present invention has been described in terms of its application to hip prosthetic implant components, as stated hereinabove, the teachings of the present invention may be applied to any prosthetic implant having an elongated portion, since the adjustability of the modulus of elasticity of an elongated portion of a prosthetic implant is a quite useful surgical tool. Examples of other such implants include intramedullary rods, stemmed knee implant components, etc.

The present invention has many advantages, including the following:

(a) the modulus of elasticity of the stem component thereof may be adjusted to approximate that of live bone adjacent thereto as implanted;

(b) the fatigue strength of the inventive stem component is in excess of the life expectancy of the host bone;

(c) approximately 90 percent of the surface area of the stem component consists of fiber metallic material thereby facilitating bony ingrowth;

(d) the head-neck portion of the inventive prosthesis may be interchangeable to allow adjustability for different surgical situations;

(e) the inventive prosthesis may be used with current acetabular cups;

(f) the inventive prosthesis may be made with or without a collar and may be implanted using current surgical instruments;

Additionally, providing a stem component with a progressive modulus of elasticity closely replicating the variable modulus of elasticity found in live healthy bone causes loads which are applied by the walking cycle to be converted to equal stresses at all points throughout the interface, thereby stimulating healthy bone formation at the ingrowth site.

As such, an invention has been disclosed in terms of preferred embodiments thereof which fulfill each and every one of the objects of the invention as set forth hereinabove and provide a new and improved implant having varying modulus of elasticity which may be applied to prosthetic components of all types in an effective manner.

Of course, various changes, modifications and alterations in the teachings of the present invention may be contemplated by those skilled in the art without departing from the intended spirit and scope thereof. As such, it is intended that the present invention only be limited by the terms of the appended claims.

I claim:

1. An implant comprising:
    (a) a shoulder having strut means depending therefrom;
    (b) a series of structures stacked on said strut means, said structures including fiber metal structures and solid metallic structures combining with said strut means to form a stem component depending from said shoulder;
    (c) said fiber metal structures and solid metallic structures being arranged in a desired relationship causing said stem component to have a modulus of elasticity which varies from one end of said stem component to another end thereof in a desired manner, and wherein the fiber metal structures and solid metallic structures are stacked in an alternating relationship and wherein the thickness of the fiber metal structures increase progressively from one end of the stem component to the other end thereof in a desired manner, such that the fiber metal structure nearest the shoulder is thinner than the fiber metal structure at the end of the stem opposite the shoulder.

2. The invention of claim 1, wherein said fiber metal structures comprise discs.

3. The invention of claim 1, wherein said fiber metal structures comprise segments.

4. The invention of claim 2, wherein said solid metallic structures comprise discs.

5. The invention of claim 3, wherein said solid metallic structures, comprise plates.

6. The invention of claim 1, wherein the implant further includes an end cap mounted at a distal end of the stem component remote from said shoulder.

7. The invention of claim 1, wherein said shoulder depends or extends from a neck portion of said prosthesis.

8. The invention of claim 1, wherein the shoulder, strut means, solid metallic structures and fiber metal structures are all made from a suitable metallic material and are all sintered together in a desired manner.

9. The invention of claim 7, wherein said neck portion has a head portion attached thereto.

10. The invention of claim 9, wherein said prosthesis comprises a hip prosthesis.

11. The invention of claim 1, wherein said stem component is made of biocompatible materials.

12. The invention of claim 11, wherein said biocompatible materials include titanium and/or alloys of titanium.

13. An implant comprising:
(a) a shoulder having strut means depending therefrom;
(b) a series of structures stacked on said strut means, said structures including fiber metal structures and solid metallic structures combining with said strut means to form a stem component depending from said shoulder;
(c) said fiber metal structures and solid metallic structures being arranged in a desired relationship causing said stem component to have a modulus of elasticity which varies from one end of said stem component to another end thereof in a desired manner, and wherein said strut means comprises a plurality of struts which comprise a main strut and a plurality of smaller diameter struts surrounding said main strut.

14. The invention of claim 13, said main strut having a distal threaded terminus, and an end cap having a threaded recess being threadably mounted on said terminus.

15. The invention of claim 13, wherein said plurality of smaller diameter struts comprises four smaller diameter struts.

16. The invention of claim 15, further including an end cap having a recess for each strut.

17. An implant comprising:
(a) a shoulder having strut means depending therefrom;
(b) a series of structures stacked on said strut means, said structures including fiber metal structures and solid metallic structures combining with said strut means to form a stem component depending from said shoulder;
(c) said fiber metal structures and solid metallic structures being arranged in a desired relationship causing said stem component to have a modulus of elasticity which varies from one end of said stem component to another end thereof in a desired manner, and wherein the fiber metal structures and solid metallic structures are stacked in an alternating relationship, and wherein the thickness of respective fiber metal structures in between each successive solid metallic structures increases as the stem component progresses in a direction away from said shoulder.

18. The invention of claim 17, wherein each said fiber metal structure between each successive solid metallic structure comprises a single fiber metal segment.

19. The invention of claim 17, wherein each said fiber metal structure between each successive solid metallic structures comprises a plurality of fiber metal discs.

20. An implant comprising:
(a) a shoulder having strut means depending therefrom;
(b) a series of structures stacked on said strut means, said structures including fiber metal structures and solid metallic structures combining with said strut means to form a stem component depending from said shoulder;
(c) said fiber metal structures and solid metallic structures being arranged in a desired relationship causing said stem component to have a modulus of elasticity which varies from one end of said stem component to another end thereof in a desired manner, and wherein said fiber metal structures comprise discs and said solid metallic structures comprise discs, and wherein said solid metallic discs and said fiber metal discs are stacked on said strut means in an alternating pattern and wherein the solid metallic discs and fiber metal discs are each substantially the same thickness and wherein the number of fiber metal discs in between each successive respective solid metallic disc increases progressive from one end of the stem component to the other end thereof in a desired manner.

21. An implant comprising:
(a) a shoulder having strut means depending therefrom;
(b) a series of structures stacked on said strut means, said structures including fiber metal structures and solid metallic structures combining with said strut means to form a stem component depending from said shoulder;
(c) said fiber metal structures and solid metallic structures being arranged in a desired relationship causing said stem component to have a modulus of elasticity which varies from one end of said stem component to another end thereof in a desired manner, and wherein said shoulder is comprised of two interconnected plate-like extensions with a chamber therebetween for receiving an upper-most fiber metal structures.

22. An implant comprising:
(a) a shoulder having strut means depending therefrom;
(b) a series of structures stacked on said strut means, said structures including porous structures and solid structures combining with said strut means to form a stem component depending from said shoulder;
(c) said porous structures and solid structures being arranged in a desired relationship causing said stem component to have a modulus of elasticity which varies from one end of said stem component to another end thereof in a desired manner, and wherein the porous structures and solid structures are stacked in an alternating relationship, and wherein the thicknesses of the porous structures increase progressively from one end of the stem component to the other end thereof in a desired manner, such that the porous structure nearest the shoulder is thinner than the porous structures at the end of the stem opposite the shoulder.

23. An implant comprising:
(a) a shoulder having strut means depending therefrom;

(b) a series of structures stacked on said strut means, said structures including porous structures and solid structures combining with said strut means to form a stem component depending from said shoulder;

(c) said porous structures and solid structures being arranged in a desired relationship causing said stem component to have a modulus of elasticity which varies from one end of said stem component to another end thereof in a desired manner, and wherein said porous structures comprise discs and said solid structures comprise discs, and wherein said solid discs and said porous discs are stacked on said strut means in an alternating pattern and wherein the solid discs and porous discs are each substantially the same thickness and wherein the number of porous discs in between each successive respective solid disc increases progressively from one end of the stem component to the other end thereof in a desired manner.

24. An implant comprising:

(a) a shoulder having strut means depending therefrom;

(b) a series of structures stacked on said strut means, said structures including fiber metal structures and solid metallic structures combining with said strut means to form a stem component depending from said shoulder;

(c) said fiber metal structures and solid metallic structures being arranged in a desired relationship causing said stem component to have a modulus of elasticity which varies from one end of said stem component to another end thereof in a desired manner, and wherein said fiber metal structures comprise discs and said solid metallic structures comprise discs, and wherein said discs are stacked on said strut means in a pattern from said shoulder comprising one fiber metal disc, one solid metallic disc, two fiber metal discs, one solid metallic disc, three fiber metal discs, one said metallic disc, four fiber metal discs, one solid metallic disc, and so on, such that the modulus of elasticity of said stem component progressively decreases in a direction away from said shoulder.

* * * * *